United States Patent [19]

Haslanger et al.

[11] Patent Number: 4,604,407
[45] Date of Patent: Aug. 5, 1986

[54] HYDROXAMATES

[75] Inventors: Martin F. Haslanger, Lambertville; Donald S. Karanewsky, East Windsor, both of N.J.

[73] Assignee: E. R. Squibb & Sons, Inc., Princeton, N.J.

[21] Appl. No.: 720,102

[22] Filed: Apr. 4, 1985

[51] Int. Cl.$^4$ ............... A61K 31/165; A61K 31/185; C07C 83/10
[52] U.S. Cl. .................. 514/575; 260/404; 260/404.5; 260/500.5 H; 260/501.1; 260/501.11; 514/555; 560/20; 560/312; 562/452
[58] Field of Search ............ 260/500.5 H, 501.1, 260/501.11, 453 RW; 514/575, 555; 560/20, 312; 562/452

[56] References Cited

U.S. PATENT DOCUMENTS

| | | | |
|---|---|---|---|
| 2,346,665 | 4/1944 | Cupery | 260/500.5 H |
| 3,247,197 | 4/1966 | Gaeumann et al. | 260/500.5 H |
| 3,398,113 | 8/1968 | Godshalk et al. | 260/500.5 H |
| 3,479,396 | 11/1969 | Buu-Hoi et al. | 260/500.5 H |
| 3,560,492 | 2/1971 | Burk et al. | 260/500.5 H |
| 3,632,764 | 1/1972 | Wakeman et al. | 514/575 |
| 3,825,585 | 7/1974 | Chappelow et al. | 260/500.5 H |
| 3,857,946 | 12/1974 | Shibata | 514/575 |
| 3,978,116 | 8/1976 | Fried et al. | 260/500.5 H |
| 4,092,430 | 5/1978 | Sallmann et al. | 260/500.5 H |
| 4,098,903 | 7/1978 | Fountain et al. | 260/500.5 H |
| 4,109,013 | 8/1978 | Grill et al. | 260/500.5 H |
| 4,188,338 | 2/1980 | Bruins et al. | 260/500.5 H |
| 4,218,478 | 8/1980 | Omura et al. | 260/500.5 H |
| 4,407,822 | 10/1983 | Lafon | 260/500.5 H |
| 4,448,730 | 5/1984 | van't Riet et al. | 260/500.5 H |
| 4,465,507 | 8/1984 | Konno et al. | 260/453 RW |
| 4,497,827 | 2/1985 | Nelson | 514/575 |

FOREIGN PATENT DOCUMENTS

| | | | |
|---|---|---|---|
| 0127726 | 12/1984 | European Pat. Off. | 260/500.5 H |
| 2290425 | 9/1976 | France | 260/500.5 H |
| 187007 | 11/1966 | U.S.S.R. | 260/500.5 H |

OTHER PUBLICATIONS

Ghosh et al, "J. Indian Chem. Soc.", vol. 46, No. 6, 1969.

Corey et al., "Rationally Designed, Potent Competitive Inhibitors of Leukotriene Biosynthesis", J. Am. Chem. Soc., 1984, 106, 1503–1504.

Primary Examiner—J. E. Evans
Attorney, Agent, or Firm—Lawrence S. Levinson; Burton Rodney

[57] ABSTRACT

Hydroxamates are provided having the structure

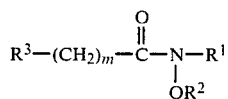

wherein $R^1$ is hydrogen, lower alkyl, aryl, lower alkenyl, cycloalkenyl, aralkyl, or

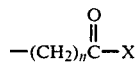

wherein n is 1 to 4 and X is hydroxy, alkoxy, amino, $C_1$–$C_4$-alkylamino or $C_1$–$C_4$-dialkylamino.
$R^2$ is hydrogen or lower alkyl; and
$R^3$ is $C_1$–$C_{20}$ alkyl or $C_3$–$C_{20}$ alkenyl, aryl, aryl-alkyl, cycloalkyl, aryl-alkenyl, lower alkoxy, lower alkenyloxy, aryl-alkoxy or cycloalkyloxy, and m is 0 to 5. These compounds are useful as inhibitors of $\Delta^5$-lipoxygenase and as such are useful as antiallergy agents.

13 Claims, No Drawings

HYDROXAMATES

DESCRIPTION OF THE INVENTION

The present invention relates to arylhydroxamates which are inhibitors of $\Delta^5$-lipoxygenase and as such are useful, for example, as antiallergy agents. These compounds have the structural formula

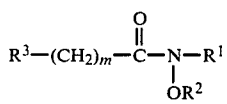

wherein $R^1$ is hydrogen, lower alkyl, aryl, lower alkenyl, cycloalkyl, aralkyl or

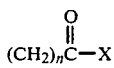

wherein n is 1 to 4 and X is hydroxy, lower alkoxy, amino, $C_1$-$C_4$-alkylamino or $C_1$-$C_4$-dialkylamino;

$R^2$ is hydrogen or lower alkyl; and $R^3$ is $C_1$-$C_{20}$ alkyl, $C_3$-$C_{20}$ alkenyl, aryl, aryl-alkyl, cycloalkyl, aryl-alkenyl, lower alkoxy, lower alkenyloxy, aryl-alkoxy or cycloalkyloxy; and m is 0 to 5.

Where $R^1$ is

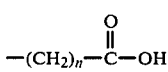

and $R^2$ is H, the above compounds may form binary or dibasic salts such as with alkali metal, such as a dilithium, disodium or dipotassium salt; where $R^1$ is other than

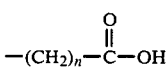

and $R^2$ is H, the above compounds will form only a monobasic salt. In addition, the compounds of formula I will form salts with dicyclohexylamine or other amines as well as with tris(hydroxymethyl)aminomethane, glucamine and other amines as set out in U.S. Pat. No. 4,294,759.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent, an alkylcycloalkyl substituent, hydroxy, an alkylamino substitutent, an alkanoylamino substituent, an arylcarbonylamino substituent, a nitro substituent, a cyano substituent, a thiol substituent or an alkylthio substituent.

The term "$C_1$-$C_{20}$ alkyl" as employed herein includes the above alkyl radicals of 1 to 8 carbons and more as well as alkyl radicals of up to and including 20 carbon atoms, preferably from 4 to 16 carbons, such as in addition to the $C_4$ to $C_{12}$ alkyl radicals set out above, tridecyl, tetradecyl, pentadecyl, hexadecyl, heptadecyl, octadecyl, nonadecyl, eicosanyl including all isomers thereof with or without the above substituents.

The term "cycloalkyl" employed herein by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, an aryl group, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and 1 or 2 alkylthio groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), 1 or 2 lower alkoxy groups, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" as employed herein by itself or as part of another group includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

The term "$C_3$-$C_{20}$ alkenyl" includes straight or branched chain radicals of from 3 to 20 carbons, preferably 4 to 16 carbons in the normal chain, which include one double bond in the normal chain, such as any of the lower alkenyl groups mentioned above as well as 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 2-tridecenyl, 3-tetradecenyl, 1-pentadecenyl, 2-hexadecenyl, 4-heptadecenyl, 7-octadecenyl, 6-nonadecenyl and 8-eicosenyl, 2,5-hexadienyl, 3,7-octadienyl, 2,6-decadienyl, 3,9-pentadecadienyl, 4,12-nonadecadienyl, including all isomers thereof and the like.

The term "aryl-alkenyl" as used herein refers to lower alkenyl groups as discussed above having an aryl substituent.

The term "lower alkoxy", "alkoxy", "lower alkenyloxy", "cycloalkoxy" or "aralkoxy" includes any of the above lower alkyl, alkyl, lower alkenyl, cycloalkyl or aralkyl groups linked to an oxygen atom.

The term "alkanoyl" as used herein by itself or as part of another group refers to a lower alkyl group linked to a carbonyl group.

The term "halogen" or "halo" as used herein refers to chlorine, bromine, fluorine or iodine with chlorine being preferred.

The terms "$(CH_2)_m$" and "$(CH_2)_n$", include a straight or branched chain radical having from 0 to 5 carbons in the normal chain in the case of "$(CH_2)_m$", and 1 to 4 carbons in the normal chain in the case of "$(CH_2)_n$" and may contain one or more lower alkyl or halo substituents. Examples of $(CH_2)_m$ and $(CH_2)_n$ groups include

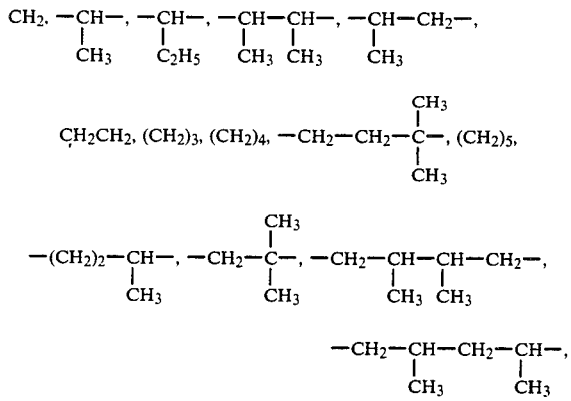

and the like.

Preferred are those compounds of the invention wherein m is 1, 2 or 3, $R^1$ is alkyl, such as methyl, pentyl, phenyl or phenylalkyl, $R^2$ is H and $R^3$ is biphenyl, cycloalkyl or phenyl.

The various compounds of the invention may be prepared as described below.

Compounds of formula I wherein $R^2$ is H may be prepared as follows.

The acid of the structure A

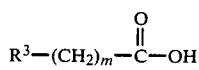  A is subjected to a coupling reaction by reacting A with an O-protected hydroxyl amine of the structure B (B) $NH_2$-O Protecting group (wherein the protecting group is benzyl, tetrahydropyranyl, methylthiomethyl or methoxymethyl) at a temperature within the range of about −15° to about 25° C., employing a molar ratio of B:A within the range of about 1:1 to about 2.5:1, in the presence of an activating catalyst such as 1-hydroxybenzotriazole and a coupling reagent such as N,N'-dicyclohexylcarbodiimide (DCC) and an organic base such as triethylamine to form hydroxamate II

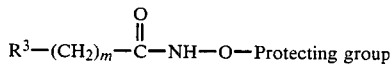  II

The hydroxamate II is then reacted with halide C (C) Hal-$R^{1a}$ (wherein Hal is I, Br or Cl and $R^{1a}$ is the same as $R^1$ where $R^1$ is to be lower alkyl, aryl, cycloalkyl, aralkyl or

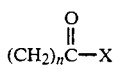

wherein X is lower alkoxy in the final product) at a temperature within the range of about 50° to about 110° C., employing a molar ratio of C:II of within the range of about 1:1 to about 3:1, in the presence of a base such as sodium hydride and an inert organic solvent such as toluene or benzene to form compound III

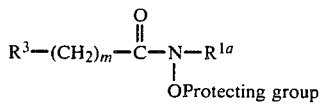  III

The protected compound III where the protecting group is benzyl is then subjected to hydrogenolysis and hydrogenation by treating compound III with hydrogen in the presence of a palladium hydroxide on carbon catalyst to form the compounds of the invention IV

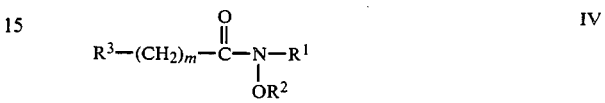  IV wherein $R^1$ is $(CH_2)_n$-$CO_2$alkyl, alkyl, aryl, cycloalkyl or aralkyl, $R^2$ is H and $R^3$ is $C_1$-$C_{20}$ alkyl or aryl-alkyl. However, where $R^1$ is to be

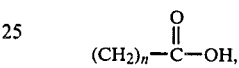

the ester group in IV may be removed by treating with an alkali metal hydroxide such as lithium hydroxide in an organic solvent such as dioxane or methanol.

Where $R^1$ in the final product is to be

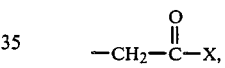

that is, n is 1, and X is OH or alkoxy, then the protected compound II will be reacted with allyl bromide ($BrCH_2CH=CH_2$) to form the intermediate IIIa

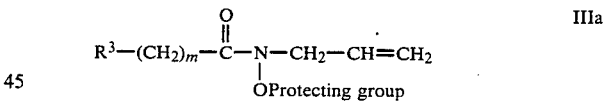  IIIa which is then treated with ozone, Jones reagent ($H_2CrO_4$/$H_2SO_4$/$H_2O$) and diazomethane to form the ester IIIb

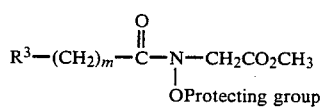  IIIb

Ester IIIb may then be subjected to hydrogenolysis as described above to form the ester IVa of the invention

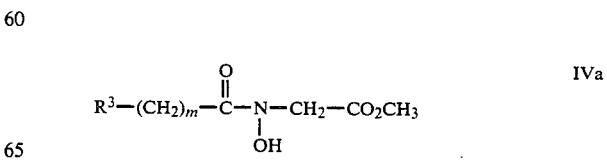  IVa which may then be hydrolyzed to the corresponding acid IVb.

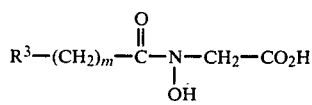
IVb

Where it is desired to form compounds wherein $R^3$ $C_3$-$C_{20}$ is alkenyl or aryl-alkenyl and/or $R^1$ is lower alkyl, the protecting group (where the protecting group is either tetrahydropyranyl or methoxymethyl) may be removed by treating III or IIIb with acetic acid without reducing the double bond in the $R^3$ group and/or in the $R^1$ group. Alternatively, when the protecting group is methylthiomethyl, it can be removed by treatment with $CuO$-$CuCl_2$ in aqueous acetone without reducing the double bond in the $R^3$ group or in the $R^1$ group.

Where it is desired to prepare compounds of the invention wherein $R^1$ is

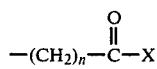

and X is amino, alkylamino or dialkylamino (wherein each alkyl of the dialkyl group is the same or different), then compound III wherein $R^1$ is

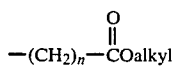

is hydrolyzed to the corresponding acid IIIA by reacting III with lithium hydroxide in the presence of a solvent such as dioxane as described above

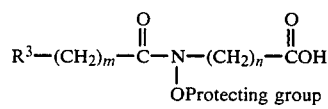
IIIA

The acid IIIA is then treated with an activating agent such as isobutylchloroformate, organic base such as triethylamine and inert organic solvent such as acetonitrile and reacted with ammonium hydroxide where X is amino or with an appropriate alkylamine or dialkylamine where X is alkylamino or dialkylamino, respectively, to form amide IIIB

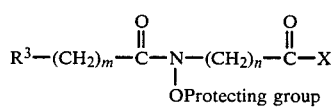
IIIB

Compound IIIB where the protecting group is benzyl may then be subjected to hydrogenolysis and hydrogenation as described above to form IVA

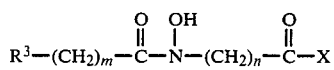
IVA ($R^3$ is alkyl and X is amino or alkylamino). Compound IIIB where the protecting group is tetrahydropyranyl may also be treated with acetic acid to remove the protecting group to form the corresponding compound wherein $R^3$ is alkenyl.

Compounds of the invention wherein $R^1$ is hydrogen may be prepared by removing the protecting group of compound II, for example, by treating II, where the protecting group is tetrahydropyranyl, with an acid catalyst such as pyridinium p-toluene sulfonate in the presence of an alcoholic solvent such as methanol, to form IIA

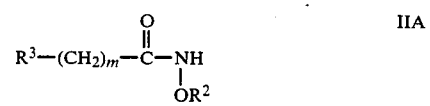
IIA (wherein $R^2$ is hydrogen) Compound IIA may be reduced as described above to form the corresponding compound wherein $R^3$ is $C_3$ to $C_{20}$ alkyl.

Preparation of compounds of formula IIA wherein $R^2$ is alkyl, that is compound V, is described hereinafter.

Compounds of the invention wherein $R^2$ is alkyl and $R^3$ is $C_1$-$C_{20}$ alkyl or aryl-alkyl may be prepared by subjecting acid A to a coupling reacting as described above except that the hydroxylamine coupling reagent employed has the structure (D) $NH_2$-O-alkyl to form the hydroxamate V

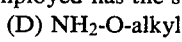
V

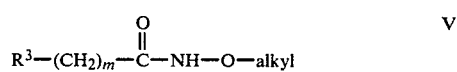

The hydroxamate V is then reacted with halide C as described above to form the compound of the invention of the structure VI

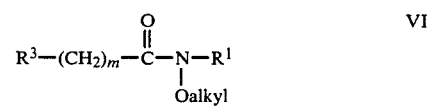
VI wherein $R^3$ is $C_3$-$C_{20}$ alkenyl or aryl-alkyl Compound VI may be reduced as described above to form the corresponding compound wherein $R^3$ is $C_3$-$C_{20}$ alkyl and/or may be hydrolyzed (where $R^1$ is

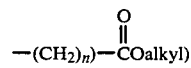

to form the corresponding acid.

Compounds of formula I wherein $R^2$ is H may also be prepared by treating the acid A

A with oxalyl chloride in the presence of an inert organic solvent such as benzene, ethyl ether or tetrahydrofuran under an inert atmosphere such as argon to form the corresponding acid chloride E

E which is then reacted with hydroxylamine F

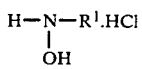

in the presence of an inert organic solvent such as tetrahydrofuran and in an organic base such as triethylamine to form the compounds of the invention IIA

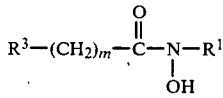

Compounds of formula I wherein $R^2$ is alkyl may be prepared from compound IIA by treating IIA with a base such as sodium hydride and an alkyl halide (Hal-Alkyl) in the presence of an inert organic solvent such as tetrahydrofuran and dimethylformamide, to form compounds of the invention VIA

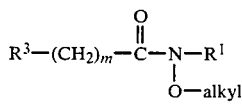

In an alternative method, compounds of formula I of the invention may be prepared by subjecting acid A to a coupling reaction by reacting acid A with an amine salt of the structure IX

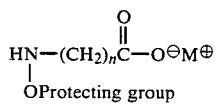

wherein the protecting group is $C_6H_5CH_2$, $CH_3SCH_2$, or tetrahydropyranyl and the like and M is an alkali metal such as Li, Na or K, or M is tetrabutylammonium, dissolved in an inert organic solvent such as dioxane, acetone, dimethylformamide or acetonitrile, in the presence of an activating agent such as isobutylchloroformate, an organic base such as triethylamine, and an inert organic solvent such as acetone, dioxane, dimethylformamide or acetonitrile. The coupling reaction is carried out at temperatures within the range of about $-15°$ to about $25°$ C., employing a molar ratio of IX:A within the range of about 1:1 to about 3:1, to form the intermediate acid of the structure X

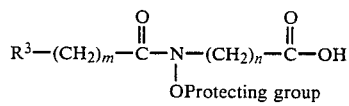

The acid X is then esterified, for example, by reacting X with a diazoalkane, such as diazomethane in ether, to form the ester XI

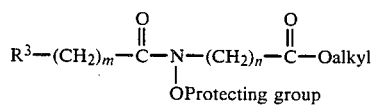

The ester XI is then subjected to a deprotecting procedure wherein XI is treated with cupric oxide and cupric chloride in an aqueous organic solvent mixture such as aqueous acetone (in the case where the protecting group is $CH_3SCH_2$—) or XI is treated with $H_2$ in the presence of a palladium hydroxide on carbon catalyst in the case where the protecting group is $C_6H_5$—$CH_2$—; the deprotected compound is then immediately hydrolyzed by treatment with lithium hydroxide or other base in the presence of an inert organic solvent such as dioxane, methanol or acetonitrile to form the acid compound of the invention of the structure XII

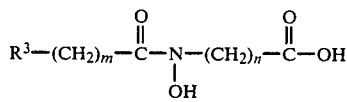

The amine salt IX may be prepared from the hydroxylamine of the structure G (G) Protecting group —$ONH_2$ by reacting G with acid halide H

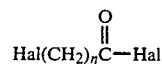

in the presence of 2,6-lutidine and methylene chloride to form the compound J

Compound J is then cyclized by reacting same with a base such as sodium hydride, in the presence of benzene to form the protected N-hydroxy lactam K

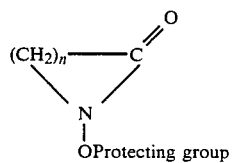

For the preparation of the lactam where the protecting group is $CH_3SCH_2$, the lactam K, where the protecting group is benzyl, can be deprotected by a hydrogenolysis reaction wherein K is treated with hydrogen in the presence of a palladium hydroxide on carbon catalyst and an inert organic solvent such as ethanol, methanol or ethyl acetate to form the hydroxy lactam XIII

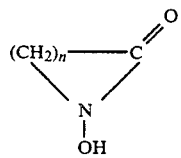

Lactam XIII can be treated with a protecting compound L (L) Hal-$CH_2SCH_3$ in the presence of weak base such as potassium carbonate or triethylamine and an inert organic solvent such as dimethyl formamide to form the protected compound XIV

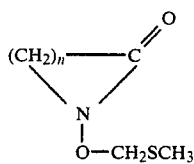

XIV

Either K or XIV is next hydrolyzed by treatment with base such as lithium hydroxide, sodium hydroxide or potassium hydroxide in the presence of dioxane to form the starting amine salt IX.

The starting acid compounds A are commercially available compounds.

The compounds of the invention are delta-5-lipoxygenase inhibitors and prevent leukotriene $C_4$ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma.

An effective but essentially non-toxic quantity of the compound is employed in treatment.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C. TLC plates were visualized by spraying and heating with 5% phosphomolybdic acid in ethanol. HP-20 refers to a high porous divinylbenzene-polystyrene polymer resin.

EXAMPLE 1

N-Hydroxy-N-methyl[1,1'-biphenylyl]-4-acetamide

To a stirring solution of 1,1'-biphenylmethyl carboxylic acid (1.0 g, 4.7 mmol) in 10 ml of dry benzene, under argon, was added oxalyl chloride (0.41 ml, 2.0 eq.). To this solution was added dimethylformamide dropwise in 10 minute intervals, until no gas was evolved and the solution turned slightly cloudy (2 drops). The mixture was stirred for 1 hour, then reduced on the rotovap without heating. The crude product was diluted with 5 ml of tetrahydrofuran and added dropwise to a 0° C. solution of N-methylhydroxylamine hydrochloride (785 mg, 2 eq.) in 20 ml of THF:H2O (1:1) with triethylamine (1.93 ml, 3.0 eq.). The solution was stirred for 0.5 hour at 0° C. then allowed to warm to room temperature and stir overnight. The reaction mixture was diluted with EtOAc and the organic layer was washed with H2O, 1N HCl (2X), and brine, then dried over anhydrous MgSO4. Concentration in vacuo gave an off-white solid which was recrystallized from hot hexane/EtOAc, to give title product (836 mg, 74%) as a yellow solid.

TLC (1:1) Hexane:EtOAc $R_f$=0.11, (UV+PMA, visualization). Product streaks to baseline.

Anal Calcd for $C_{15}H_{15}NO_2$: C, 74.67; H, 6.27; N, 5.81. Found: C, 74.62; H, 6.28; N, 5.68

EXAMPLE 2

N-(1,1-Dimethylethyl)-N-hydroxy[1,1'-biphenylyl]-4-acetamide

To a stirring solution of 1,1'-biphenylmethylcarboxylic acid (500 mg, 2.36 mmol) in 10 ml of dry benzene under argon, was added oxalyl chloride (0.23 ml, 2.0 eq.). To this solution was added dimethylformamide dropwise in 10 minute intervals, until no gas was evolved and the solution turned slightly cloudy (2 drops). The mixture was stirred for 1 hour, then reduced on the rotovap without heating. The crude product, a white solid, was dissolved in 5 ml tetrahydrofuran and added dropwise to a 0° C. solution of N-t-butylhydroxylamine hydrochloride (593 mg, 2 eq.) in 20 ml of THF:H2O (1.1) with triethylamine (1.0 ml, 3.0 eq.). The solution was stirred for 1 hour at 0° C., then allowed to warm to room temperature and stir overnight. The reaction mixture was diluted with EtOAc and the organic layer was washed with H2O, 1N HCl (2X), and brine, then dried over anhydrous MgSO4. Concentration in vacuo gave an oil, which upon standing a crystal formed. This solid was recrystallized from hot hexane/EtOAc, to give title product, 69 mg (10%), as long light yellow needles.

TLC (1:1) Hexane:EtOAc $R_f$0.40, UV+CeMo. Product streaks to baseline.

Anal Calcd for $C_{18}H_{21}NO_4$: C, 76.30; H, 7.47; N, 4.94. Found: C, 76.43; H, 7.63; N, 4.81.

EXAMPLE 3

N-Hydroxy-N-phenylbenzenebutanamide

To a stirring solution of 3-phenylpropylcarboxylic acid (500 mg, 3.1 mmol) in 10 ml of dry benzene under argon was added oxalyl chloride (0.30 ml, 1.1 eq.). To this solution was added dimethylformamide dropwise in 10 minute intervals, until no gas was evolved and the solution turned slightly cloudy (2 drops). The mixture was stirred for 1 hour then reduced on the rotovap without heating. The crude product was diluted with 5 ml of tetrahydropyran and added dropwise to a 0° C. solution of N-phenylhydroxylamine (666 mg, 2 eq.) in 20 ml of THF:H2O (1:1) with triethylamine (0.85 ml, 2.0 eq.). The solution was stirred for 1 hour at 0° C. then allowed to warm to room temperature and stir overnight. The reaction mixture was diluted with EtOAc and the organic layer was washed with H2O, 1N HCl (2X), and brine, then dried over anhydrous MgSO4. Concentration in vacuo gave a white solid which was recrystallized from hot hexane/EtOAc, to give title product (451 mg, 58%) as a flat golden crystalline solid.

TLC (1:1) Hexane:EtOAc $R_f$=0.47, UV+CeMo

Anal Calcd for $C_{16}H_{17}NO_2$: C, 75.27; H, 6.71; N, 5.49. Found: C, 75.55; H, 6.71; N, 5.30.

EXAMPLE 4

N-Hydroxy-N-(phenylmethyl)cyclohexaneacetamide

A. 0-Tetrahydropyran-2-ylhydroxylamine ($H_2N$-OTHP)

With gentle heating N-hydroxyphthalimide (10.0 g, 61.4 mM) was dissolved in dry $CH_2Cl_2$ (70 ml) and dioxane (80 ml), then dihydropyran (6.16 ml, 67.6 mM, 1.1 eq) and p-toluenesulfonic acid monohydrate (200 mg, 2% by weight) were added and the mixture stirred for 2 hours at room temperature under argon. The mixture was then washed successively with saturated $NaHCO_3$ (2X) and brine, dried over anhydrous $Na_2SO_4$ and evaporated to a white solid. The solid was triturated with hexane and filtered to give 13.43 g (89%) of O-tetrahydropyranyl hydroxyphthalimide as a white solid m.p. 123°–125° C. with consistent NMR (60 MHz, $CDCl_3$) spectral data. TLC (1:1) EtOAc-Hex, $R_f$=0.75, UV+PMA.

To a stirred solution of the O-THP hydroxyphthalimide (13.0 g, 52.6 mM) in dry benzene (30 ml) was added methyl hydrazine (2.82 ml, 53.0 mM) and the mixture heated at 80° C. for 15 minutes under argon. The mixture was concentrated to a 50 ml volume then vacuum distilled to give 5.46 g (89%) of the desired THP-hydroxylamine as a clear colorless oil with b.p.=70° C. (10 mm Hg). Note: Compound crystallizes upon cooling in freezer under argon. TLC (1:1) EtOAc-Hex, $R_f$0.31, UV+PMA.

B. N-(Tetrahydropyran-2-yloxy)cyclohexaneacetamide

To a 0° C. solution of cyclohexanemethylcarboxylic acid (1.0 g, 7.0 mmol) in 40 ml of $C_2Cl_2$ under argon was added O-tetrahydropyran-2-ylhydroxylamine (1.64 g, 2.0 eq.), 1-hydroxybenzotriazole (1.14 g, 1.2 eq.), N,N'-dicyclohexylcarbodiimide (1.73 g, 1.2 eq.) sequentially. After 0.5 hour at 0° the solution was allowed to warm to room temperature and stir under argon for 6 hours. The solution was filtered, concentrated in vacuo to yield a white solid which was chromatographed on LPS-1 silica gel eluting with 1:1 hexane/EtOAc. Product containing fractions were evaporated to give title compound, a white solid 1.05 g (62%) after trituration with hexane.

C. N-(Phenylmethyl)-N-(tetrahydropyran-2-yloxy)cyclohexaneacetamide

To a stirring solution of the compound of Part B (500 mg, 2.1 mmol) under argon in 10 ml of dry toluene was added NaH (1.1 eq., 55 mg). The mixture was allowed to stir for 30 minutes then benzyl bromide (0.74 ml, 3.0 eq.) was added. The mixture was heated to reflux and allowed to stir for 2 hours. The reaction was cooled and diluted with EtOAc and partitioned over 5% $KHSO_4$. The organic phase was washed with brine, dried over anhydrous $MgSO_4$ and evaporated to yield yellow oil which was chromatographed on LPS-1 silica gel eluting with 9:1 hexane:EtOAc. Product containing fractions were evaporated to give title compound (560 mg, 82%) as a pale yellow oil. TLC (9:1) hexane:EtOAc. $R_f$=0.19, UV+CeMO.

D. N-Hydroxy-N-(phenylmethyl)cyclohexaneacetamide

To a stirring solution of the compound of Part C (560 mg, 1.7 mmol) in 10 ml of $CH_3OH$ under argon was added pyridinium-p-toluenesulfonate (510 mg; 1.2 eq.). The solution was heated to 60° C. in an oil bath for 24 hours. The solution was diluted with EtOAc and washed with 10 ml of brine, diluted with 10 ml of water. The organic layer was washed with brine (10 ml) and dried over $MgSO_4$ (anhydrous) and reduced in vacuo to yield an off-white solid which was recrystallized from hexane/EtOAc to give title product (380 mg) (91%) as a white solid with m.p. 83°–85° C. TLC (1:1) hexane-EtOAc; $R_f$=0.45, UV+CeMo.

Anal Calcd for $C_{15}H_{21}NO_2 \cdot 0.1MH_2O$: C, 72.28; H, 8.57; N, 5.62. Found: C, 72.28; H, 8.49; N, 5.51.

EXAMPLE 5

N-Hydroxy-N-(phenylmethyl)benzenebutanamide

A. N-(Tetrahydropyran-2-yloxy)benzenebutanamide

To a 0° C. solution of 3-phenylpropyl carboxylic acid (1.0 g, 6.1 mmol) in 40 ml of $CH_2Cl_2$ under argon was added $H_2N$-OTHP (1.43 mg, 2.0 eq.), 1-hydroxybenzotriazole (987 mg, 1.2 eq.), N,N'-dicyclohexylcarbodiimide (1.51 g, 1.2 eq.) sequentially. After 0.5 hour at 0°, the solution was allowed to warm to room temperature and stir under argon for 4 hours. The solution was filtered, concentrated in vacuo to yield title compound as a white solid, wt. 1.13 g (71%).

B. N-(Phenylmethyl)-N-(tetrahydropyran-2-yloxy)benzenebutanamide

To a stirring solution of Part A compound (520 mg, 197 mmol) under argon in 10 ml of dry toluene was added NaH (1.1 eq., 52 mg). The mixture was allowed to stir for 30 minutes, then benzyl bromide (0.71 ml, 3.0 eq.) was added. The mixture was heated to reflux and allowed to stir for 2 hours. The reaction was cooled and diluted with EtOAc and partitioned over 5% $KHSO_4$. The organic phase was washed with brine, dried over anhydrous $Na_2SO_4$ and evaporated to yield a yellow oil which was chromatographed on LPS-1 silica gel eluting with 4:1 hexane:EtOAc. Product containing fractions were evaporated to give title compound (550 mg, 79%) as a pale yellow oil. TLC (9:1) hexane:EtOAc. $R_f$=0.12, UV+PMA.

C. N-Hydroxy-N-(phenylmethyl)benzenebutanamide

To a stirring solution of Part B compound (550 mg, 1.55 mmol) in 10 ml of $CH_3OH$ under argon was added pyridinium-p-toluenesulfonate (391 mg, 1.0 eq.). The solution was heated to 60° C. in an oil bath for 48 hours. The solution was diluted with EtOAc and washed with 10 ml of brine, diluted with 10 ml of water. The organic layer was washed with brine (10 ml) and dried over $MgSO_4$ (anhydrous) and reduced in vacuo to yield an off-white solid, which was recrystallized from hexane/EtOAc to give title product (320 mg) (87%) as a white solid with m.p. 72°–74° C. TLC (1:1) hexane-EtOAc; $R_f$=0.38, UV+CeMo. Products streaks to baseline.

Anal Calcd for $C_{17}H_{19}NO_2 \cdot 0.11M\ H_2O$: C, 75.23; H 7.14; N, 5.16. Found: C, 75.23; H, 7.11; N, 5.20.

EXAMPLE 6

N-Hydroxy-N-pentylbenzenebutanamide

A. N-(Tetrahydropyran-2-yloxy)benzenebutanamide

To a 0° C. of 3-phenylpropyl carboxylic acid (1.0 g, 6.1 mmol) in 20 ml of $CH_2Cl_2$ under argon was added H₂N-OTHP (1.43 g, 2.0 eq.), 1-hydroxybenzotriazole (987 mg, 1.2 eq.), N,N'-dicyclohexylcarbodiimide (1.51 g, 1.2 eq.) sequentially. The solution was allowed to warm to room temperature and stir under argon for 4 hours. The solution was filtered, concentrated in vacuo, diluted with EtOAc, and refiltered. Concentration in vacuo gave a golden oil which was chromatographed on LPS-1 silica gel eluting with 1:1 hexane/EtOAc. Product containing fractions were concentrated in vacuo as a white solid which was triturated with hexane (2X) to yield title compound, wt. 1.13 g (71%).

B. N-Pentyl-N-(tetrahydropyran-2-yloxy)benzenebutanamide

To a stirring solution of Part A compound (610 mg, 2.3 mmol) under argon in 15 ml of dry toluene was added NaH (1.1 eq., 61 mg). The mixture was allowed to stir for 30 minutes then pentyl bromide (0.86 ml, 3.0 eq.) was added. The mixture was heated to reflux and allowed to stir overnight. The reaction was cooled and diluted with EtOAc and partitioned over 5% KHSO₄. The organic phase was washed with brine, dried over anhydrous MgSO₄ and evaporated to yield yellow oil which was chromatographed on LPS-1 silica gel eluting with (8:2) hexane:EtOAc. Product containing fractions were evaporated to give title compound (480 g) as an oil. TLC (1:1) hexane:EtOAc. $R_f=0.55$, UV+PMA.

C. N-Hydroxy-N-pentylbenzenebutanamide

To a stirring solution of Part B compound (480 mg, 1.44 mmol) in 15 ml of CH₃OH under argon was added pyridinium-p-toluenesulfonate (444 mg, 1.0 eq.). The solution was heated to 60° C. in an oil bath overnight. The solution was diluted with EtOAc and washed with 10 ml of brine diluted with 10 ml of water. The organic layer was washed with brine (10 ml) and dried over Na₂SO₄ (anhydrous) and reduced in vacuo to yield an oil which was chromatographed on LPS-1 silica gel eluting with 1:1 hexane/EtOAc. Product containing fractions were evaporated to give title product 360 mg (~100%). TLC (1:1) hexane/EtOAc $R_f=0.29$, UV+-PMA. Product streaks to baseline.

Anal Calcd for C₁₅H₂₃NO₂·0.22M H₂O: C, 71.10; H, 9.32; N, 5.53. Found: C, 71.10; H, 9.11; N, 5.20.

EXAMPLE 7

N-Hydroxy-N-methyldecaneamide

A. N-Benzyloxy-1-decenylamide

To a stirred solution of the 1-decenyl carboxylic acid (2.00 g, 11.64 mM) in dry CH₂Cl₂ (35 ml) is added 1-hydroxybenzotriazole (1.89 g, 13.97 mM, 1.2 eq.) and N,N'-dicyclohexylcarbodiimide (2.88 g, 13.97 mM, 1.2 eq.). After one hour at room temperature under argon, O-benzylhydroxylamine hydrochloride (4.64 g, 29.1 mM, 2.5 eq.) and Et₃N (4.06 ml, 29.1 mM, 2.5 eq.) are added and the mixture stirred for an additional two hours. The crude mixture is filtered (2X), evaporated, taken up in ethyl acetate, filtered again and then washed successively with 5% KHSO₄, saturated NaHCO₃, and brine. Concentration in vacuo leaves a solid which is flash chromatographed on LPS-1 silica gel eluting with (9:1) Hex-EtOAc. Product containing fractions are concentrated in vacuo to a white solid which is recrystallized once from ethyl acetate-hexane to give desired title product.

B. N-Benzyloxy-N-methyl-1-decenylamide

To a solution of the title A benzylhydroxamate (496 mg, 1.80 mM) in dry toluene (5 ml) is added prewashed NaH (45 mg, 1.80 mM) and the mixture stirred for 20 minutes at room temperature under argon. Excess methyl iodide (0.313 ml, 4.92 mM, 3 eq) is added and the mixture is refluxed for 5 hours, then cooled and partitioned between 5% KHSO₄ and ethyl acetate. The organic phase is washed with brine, dried over anhydrous Na₂SO₄ and evaporated to a yellow oil which was chromatographed on Whatman LPS-1 silica gel eluting with (3:2) pet ether-ether. Product containing fractions are evaporated to give the title N-methylated product.

C. N-Hydroxy-N-methyldecaneamide

Argon is bubbled through a solution of the title B N-methylhydroxamate (600 mg) in CH₃OH (10 ml) for 5 minutes before adding 20% palladium hydroxide on carbon (100 mg, 15% by weight) and stirring under H₂ for 2 hours. The mixture is then filtered through Celite, evaporated, taken up in EtOAc, filtered through a small plug of Whatman LPS-1 silica gel and evaporated to an off-white crystalline solid. Recrystallization from EtOAc-Hex gives desired title product.

EXAMPLE 8

4-[(1-Decenylcarbonyl)hydroxyamino]butanoic acid

A. N-(Tetrahydropyran-2-yloxy)-1-decenylamide

To a solution of 1-decenylcarboxylic acid (0.66 g, 3.84 mM) in dry CH₂Cl₂ (15 ml) is added 1-hydroxybenzotriazole (623 mg, 4.61 mM, 1.2 eq) and DCC (951 mg, 4.61 mM, 1.2 eq) and the mixture stirred for one hour under argon at room temperature. O-THP-hydroxylamine (900 mg, 7.68 mM, 2 eq) is added and the mixture stirred for 3 hours at room temperature. The mixture is filtered, evaporated, taken up in ethyl acetate, filtered again, evaporated and chromatographed on Whatman LPS-1 silica gel eluting with (8:2) Hex-EtOAc. Product containing fractions are evaporated to give title coupled product.

B. 4-[(1-Decenylcarbonyl)tetrahydropyran-2-yloxyamino]butanoic acid, ethyl ester Prewashed NaH (70 mg, 2.9 mM, 1.2 eq) is added to a solution of the title A THP-hydroxamate (622 mg, 2.42 mM) in dry toluene (10 ml) and the mixture stirred at room temperature under argon for 15 minutes. Ethyl-4-iodobutyrate (1.76 g, 7.26 mM, 3 eq) is added and the mixture is refluxed overnight. The mixture is partitioned between 5% KHSO₄ and EtOAc, the organic phase washed with brine, dried over anhydrous Na₂SO₄ and evaporated to an oil. The crude oil is run through neutral alumina (act=1) to remove any remaining starting material eluting with (8:2) Hex-Acetone. Product fractions are evaporated and then chromatographed on Whatman LPS-1 silica gel eluting with (95:5) Hex-Acetone. Product fractions are evaporated to give the desired title N-alkylated product.

C. 4-[(1-Decenylcarbonyl)hydroxyamino]butanoic acid, ethyl ester

A stirred mixture of the title B O-THP hydroxamate (816 mg, 2.20 mM) in (3:2:2) HOAc:THF:H₂O (6 ml) is heated at 55° C. overnight under argon. The mixture is then carefully partitioned between saturated NaHCO₃ and EtOAc, the organic layer washed with brine, dried over anhydrous Na₂SO₄ and evaporated to give the desired title hydroxamic acid.

D. 4-[(1-Decenylcarbonyl)hydroxyamino]butanoic acid

To a solution of the title C crude ethyl ester (879 mg) in dioxane (10 ml) is added a 1.0 N LiOH solution (4.4 ml) and the mixture stirred for 1.5 hours at room temperature under argon. The mixture is then partitioned between 5% KHSO₄ and EtOAc, the organic phase washed with brine, dried over anhydrous Na₂SO₄ and evaporated to a solid. One recrystallization from EtOAc-Hex gives the desired hydroxamic acid.

EXAMPLE 9

4-[(Decylcarbonyl)hydroxyamino]butanoic acid, ethyl ester

Argon was bubbled through a solution of the Example 8 title C hydroxamate (357 mg, 1 mM) in absolute EtOH (15 ml) for 5 minutes before adding 20% palladium hydroxide on carbon (59 mg) and shaking the mixture under H₂ on a Parr apparatus for 7 hours. The mixture is filtered through a layered plug of Celite and Whatman LPS-1 silica gel and evaporated to give the desired title hydroxamic acid.

EXAMPLE 10

4-[(2-Decylcarbonyl)hydroxyamino]butanoic acid, dilithium salt

To a stirred solution of the Example 9 methyl ester (357 mg, 1 mM) in dioxane (4 ml) is added a 1.00N LiOH solution (2.6 ml, 2.6 mM) and the mixture stirred under argon for 3 hours. The mixture is diluted with H₂O, extracted with ether (to remove a non-polar impurity), the aqueous layer acidified to pH 2 with 1.0N HCl and then re-extracted with ethyl acetate. The organic phase is washed with brine, dried over anhydrous Na₂SO₄ and evaporated to an oil.

The crude oil is dissolved in 1.0N LiOH (3 ml) and chromatographed on HP-20 eluting with a gradient of neat H₂O →(50:50) H₂O-CH₃CN. Product containing fractions are combined and lyophilized to give the desired title product.

EXAMPLE 11

4-[(Decylcarbonyl)hydroxyamino]butanoic acid, ethyl ester

A. 4-[[(1-Decenyl)carbonyl]benzyloxyamino]butanoic acid, ethyl ester

Prewashed sodium hydride (188 mg, 7.52 mM, 1.1 eq.) is added to a solution of hydroxamate prepared in Example 7 Part A (2.00 g, 6.84 mM) in dry toluene (14 ml) and the mixture stirred at room temperature under argon for 15 minutes. Ethyl-4-iodobutyrate (3.31 g, 13.68 mM, 2.0 eq.) is then added and the mixture refluxed overnight. The crude mixture is cooled, partitioned between 5% KHSO₄ and EtOAc, the organic layer washed with brine, dried over anhydrous Na₂SO₄ and evaporated to an oil. The oil is dissolved in CH₂Cl₂ and flash chromatographed on Whatman LPS-1 silica gel eluting with (3:2) pet ether-ether. Product containing fractions are evaporated to give the desired title alkylated product.

B. 4-[(Decylcarbonyl)hydroxyamino]butanoic acid, ethyl ester

Argon is bubbled through a solution of the title A hydroxamate (407 mg, 1 mM) in absolute ethanol (10 ml) for 5 minutes before adding 20% palladium hydroxide on carbon (58 mg), and stirring under H₂ for 4 hours. The mixture is then filtered through a layered plug of Celite over LPS-1 silica gel, evaporated to a solid and recrystallized from EtOAc-Hex to give the desired title hydroxamic acid

EXAMPLE 12

4-[[(1-Decenyl)carbonyl]methoxyamino]butanoic acid, dicyclohexylamine salt(1:1)

A. N-methoxy-1-decenylamide

To a solution of 1-decenyl carboxylic acid (1.32 g, 7.68 mM) in dry CH₂Cl₂ (20 ml) is added 1-hydroxybenzotriazole (1.25 g, 9.22 mM, 1.2 eq.) and N,N'-dicyclohexylcarbodiimide (1.90 g, 9.22 mM, 1.2 eq.) and the mixture stirred for 1 hour at room temperature. Methoxylamine hydrochloride (1.28 g, 15.36 mM. 2 eq.) and triethylamine (2.14 ml, 15.36 mM, 2 eq.) are added, the mixture stirred for 3 hours at room temperature, then filtered, evaporated, taken up in ethyl acetate and filtered again. The organic phase is washed successively with 5% KHSO₄, saturated NaHCO₃ and brine, then dried over anhydrous Na₂SO₄ and evaporated to an oil. The crude oil is flash chromatographed on LPS-1 silica gel eluting with (7:3) hexane-ethyl acetate. Product containing fractions are evaporated to give the desired title product.

B. 4-[[(1-Decenyl)carbonyl]methoxyamino]butanoic acid, ethyl ester

To a solution of the title A methyl hydroxamate (328 mg, 1.52 mM) in dry toluene (6 ml) is added prewashed NaH (38 mg, 1.52 mM) and the mixture stirred for 20 minutes at room temperature. Ethyl-4-iodobutyrate (668 mg, 2.76 mM) is added and the mixture is refluxed overnight under argon. The mixture is cooled, partitioned between 5% KHSO₄ and ethyl acetate and the organic phase washed with brine, dried over anhydrous Na₂SO₄ and evaporated to an oil. The crude oil is flash chromatographed on LPS-1 silica gel eluting with (3:2) petroleum ether-Et₂O. Product containing fractions are evaporated to give the desired title N-alkylated product.

C. 4-[[(1-Decenyl)carbonyl]methoxyamino]butanoic acid

To a solution of the title B ethyl ester (660 mg, 2 mM) in dioxane (10 ml) is added 1.0N LiOH (2.20 ml) and the mixture stirred at room temperature under argon for two hours. The mixture is then partitioned between 5% KHSO₄ and ethyl acetate, the organic phase washed with brine, dried over anhydrous Na₂SO₄ and evaporated to an oil. Crude oil is flash chromatographed on LPS-1 silica gel eluting successively with (85–15) Hex-Acetone and (95–5) CH₂Cl₂-CH₃OH. Product containing fractions are evaporated to give the title acid.

D. 4-[[(1-Decenyl)carbonyl]methoxyamino]butanoic acid, dicyclohexylamine salt(1:1)

The dicyclohexylamine salt is prepared by dissolving the title C acid in EtOAc (1 ml) and treating it with dicyclohexylamine (126μl, 1.1 eq.). The mixture is evaporated and then crystallized from cold petroleum ether to give the title methyl hydroxamate as the dicyclohexylamine salt.

EXAMPLE 13

N-(4-Amino-4-oxobutyl)-4-decyl-N-hydroxydecaneamide

A. 4-[[(1-Decenyl)carbonyl]benzyloxyamino]butanoic acid

To a solution of the ethyl ester prepared as described in Example 11 Part A (814 mg, 2 mM) in dioxane (5 ml) is added 1.0N LiOH (2.3 ml) and the mixture stirred for 3 hours under argon at room temperature. The mixture is then partitioned between 5% $KHSO_4$ and EtOAc, the organic layer washed with brine, dried over anhydrous $Na_2SO_4$ and evaporated to give the title acid.

B. N-(4-Amino-4-oxobutyl)-4-(1-decenyl)-N-benzyloxydecaneamide

To a solution of the title A acid (379 mg, 1 mM) and $Et_3N$ (181µl, 1.3 mM) in dry $CH_3CN$ (5 ml) is added isobutylchloroformate (169µl, 1.3 mM) and the mixture stirred for 1 hour at room temperature under argon. Concentrated $NH_4OH$ (3 ml) is added dropwise, the mixture is stirred for 30 minutes, then it is partitioned between 1.0N HCl and EtOAc. The organic layer is washed with brine, dried over anhydrous $Na_2SO_4$ and evaporated to an oil. The crude oil is chromatographed on alumina (neutral activity=2) with (1:1) EtOAc-Hex and (9:1) $CH_2Cl_2$-$CH_3OH$ followed by a chromatography on Whatman LPS-1 silica gel eluting with neat EtOAc. Product containing fractions are evaporated to give the title amide.

C. N-(4-Amino-4-oxobutyl)-4-decyl-N-hydroxydecaneamide

Argon is bubbled through a solution of the title B hydroxamate (290 mg) in $CH_3OH$ (5 ml) for 5 minutes before adding 20% palladium hydroxide on carbon (35 mg, 12% by weight) and stirring under $H_2$ for 2 hours. The mixture is filtered through Celite, evaporated, taken up in EtOAc, filtered through anhydrous $MgSO_4$ powder and evaporated to an off-white solid. Two recrystallizations (from EtOAc-Hex, then acetone-Hex) give the title amide.

EXAMPLE 14

5-[(Decylcarbonyl)hydroxyamino]pentanoic acid

A. 5-[[(1-Decenyl)carbonyl]benzyloxyamino]pentanoic acid, ethyl ester

Prewashed NaH (51 mg, 2.11 mM, 1.1 eq.) is added to a solution of the hydroxamate prepared as described in Example 7 Part A (562 mg, 1.92 mM) in dry toluene (10 ml) and the mixture stirred for 20 minutes at room temperature under argon. Ethyl-5-iodovalerate (1.48 g, 5.76 mM, 3 eq.) is added and the mixture refluxed overnight. The mixture is then partitioned between 5% $KHSO_4$ and EtOAc, the organic layer washed with brine, dried over anhydrous $Na_2SO_4$ and evaporated to an oil. The remaining starting material is removed by chromatographing on neutral alumina (act. = 1) eluting with (1:1) petroleum-ether. Product fractions are evaporated, then flash chromatographed on Whatman LPS-1 silica gel eluting with (3:2) petroleum ether-ether. Product fractions are evaporated to give the title N-alkylated product.

B. 5-[(4-Decylcarbonyl)hydroxyamino]pentanoic acid, ethyl ester

Argon is bubbled through a solution of the title A hydroxamate (421 mg) in methanol (10 ml) for 5 minutes, then 20% palladium hydroxide on carbon (15 mg) is added and the mixture stirred under $H_2$ for 1 hour. The mixture is filtered through Celite, evaporated, taken up in ethyl acetate, filtered through powdered anhydrous $MgSO_4$ and evaporated to give the desired title hydroxamic acid.

C. 5-[(Decylcarbonyl)hydroxyamino]pentanoic acid

To a solution of the title B ethyl ester (331 mg, 1 mM) in dioxane (8 ml) is added 1.0 N LiOH (2.9 ml) and the mixture stirred under argon at room temperature for 40 minutes. The mixture is then partitioned between 5% $KHSO_4$ and EtOAc, the organic phase washed with brine, dried over anhydrous $Na_2SO_4$ and evaporated to a solid. One recrystallization from EtOAc-Hex gives desired title acid.

EXAMPLE 15

(N-Hydroxydecaneamido)acetic acid

A. Decyl carboxylic acid

Argon is bubbled through a solution of 1-decenylcarboxylic acid (1.6 g) in $CH_3OH$ (20 ml) for 5 minutes. 10% Palladium on carbon is added and the mix is shaken on a Parr apparatus for 4 hours under $H_2$. The mixture is filtered through Celite and evaporated to give the desired title saturated acid.

B. N-Benzyloxydecaneamide

To a solution of the title A acid (590 mg, 3.43 mM) in dry $CH_2Cl_2$ (15 ml) is added 1-hydroxybenzotriazole (557 mg, 4.12 mM, 1.2 eq.) and N,N'-dicyclohexylcarbodiimide (850 mg, 4.12 mM, 1.2 eq.) and the mixture stirred at room temperature under argon for 1 hour. Triethylamine (1.20 ml, 8.58 mM, 2.5 eq.) and O-benzylhydroxylamine hydrochloride (1.37 g, 8.58 mM, 2.5 eq.) are then added and the mixture stirred for 3 hours at room temperature. The mixture is filtered, evaporated, taken up in ethyl acetate and washed successively with 5% $KHSO_4$ and brine then dried over anhydrous $Na_2SO_4$ and evaporated to a white solid. Crude solid is flash chromatographed on Whatman LPS-1 silica gel eluting with (9:1) hexane-EtOAc. Product containing fractions are evaporated to give the desired title benzylhydroxamate.

C. N-(3-Prop-1-enyl)-N-benzyloxy decaneamide

To a solution of the title B benzylhydroxamate (399 mg, 1.36 mM) in dry toluene (6 ml) is added prewashed NaH (36 mg, 1.50 mM, 1.1 eq.) and the solution stirred at room temperature for 20 minutes before adding allyl bromide (294 µl, 3.4 mM, 2.5 eq.) and refluxing overnight. The mixture is cooled, partitioned between 5% $KHSO_4$ and EtOAc, the organic layer washed with brine, dried over anhydrous $Na_2SO_4$ and evaporated to a yellow oil. Crude oil is chromatographed on neutral alumina (act.=1) eluting with (1:1) petroleum ether-ether. Product fractions are evaporated to give the title N-alkylated product.

D. N-Benzyloxydecaneamido)acetic acid, methyl ester

The title C N-alkylbenzylhydroxamate (3.34 g, 10 mM) is dissolved in EtOAc, (16 ml) cooled to −78° C. and purged with $O_2$ before bubbling ozone through the solution until a pale blue color persisted. Excess ozone is purged with bubbling $N_2$, then the ozonide solution is treated with Jones reagent (1.0 ml) at −78° C. The mixture is allowed to warm to room temperature, diluted with EtOAc and the organic phase washed successively with $H_2O$ and brine, then dried over anhydrous $Na_2SO_4$ and evaporated to a crude oil.

The crude oil is dissolved in $Et_2O$ (10 ml), cooled to 0° C. (ice bath) and treated with an ethereal solution of diazomethane. The mixture is evaporated, and chromatographed on Whatman LPS-1 silica gel eluting with (9:1) Hex-EtOAc. Product fractions are evaporated to give of the desired title methyl ester.

E. (N-Hydroxydecaneamido)acetic acid, methyl ester

Argon is bubbled through a solution of the title D benzylhydroxamate (270 mg) in $CH_3OH$ (8 ml) for 5 minutes, then 20% palladium hydroxide on carbon (32 mg, 12% by weight) is added and the mixture stirred for 1 hour under $H_2$. The mixture is filtered through Celite, evaporated, taken up in EtOAc, filtered through anhydrous $MgSO_4$ and evaporated to give the title E hydroxamic acid.

F. (N-Hydroxydecaneamide)acetic acid

To a solution of the title E methyl ester (274 mg, 1 mM) is dissolved in dioxane (6 ml) is added 1.0N LiOH (2.16 ml, 2.16 mM) and the mixture stirred for 20 minutes at room temperature under argon. The mixture is partitioned between 5% $KHSO_4$ and EtOAc, the organic phase washed with brine, dried over anhydrous $Na_2SO_4$ and evaporated to an off-white solid. One recrystallization from EtOAc-Hex gives the desired title acid.

EXAMPLE 16

N-Hydroxy-N-propyl[1,1'-biphenylyl]-4-acetamide

Following the procedure of Example 1 except substituting N-propylhydroxylamine for N-methylhydroxylamine, the title compound is obtained.

EXAMPLE 17

N-Hydroxy-N-(phenylmethyl)[1,1'-biphenylyl]-4-acetamide

Following the procedure of Example 1 except substituting N-(phenylmethyl)hydroxylamine for N-methylhydroxylamine, the title compound is obtained.

EXAMPLE 18

N-Hydroxy-N-phenyl[1,1'-biphenylyl]-4-acetamide

Following the procedure of Example 1 except substituting N-(phenyl)hydroxylamine for N-methylhydroxylamine, the title compound is obtained.

EXAMPLE 19

N-Cyclohexyl-N-hydroxycyclohexaneacetamide

Following the procedure of Example 4 except substituting cyclohexyl iodide for benzyl bromide, the title compound is obtained.

EXAMPLE 20

N-Hydroxy-N-propylcyclohexaneacetamide

Following the procedure of Example 4 except substituting propyl iodide for benzyl bromide, the title compound is obtained.

EXAMPLE 21

N-Hydroxy-N-butylbenzenebutanamide

Following the procedure of Example 5 except substituting butyl iodide for benzylbromide, the title compound is obtained.

EXAMPLE 22

N-Hydroxy-N-i-butylbenzenebutanamide

Following the procedure of Example 5 except substituting i-butyl iodide for benzyl bromide, the title compound is obtained.

EXAMPLE 23

N-Hydroxy-N-pentylbenzenebutanamide

Following the procedure of Example 5 except substituting pentyl iodide for benzyl bromide, the title compound is obtained.

EXAMPLE 24

N-Hydroxy-N-hexylbenzenebutanamide

Following the procedure of Example 6 except substituting hexyl iodide for pentyl bromide, the title compound is obtained.

EXAMPLE 25

N-Hydroxy-N-phenethylbenzenebutanamide

Following the procedure of Example 6 except substituting phenethyl bromide for pentyl bromide, the title compound is obtained.

EXAMPLE 26

N-Hydroxy-N-octylbenzenebutanamide

Following the procedure of Example 6 except substituting octyl iodide for pentyl bromide, the title compound is obtained.

EXAMPLE 27

N-Hydroxy-benzenebutanamide

Following the procedure of Example 6 except eliminating Step B, the title product is obtained.

EXAMPLE 28

N-Hydroxy-N-methoxy-benzenebutanamide

Following the procedure of Example 3 except substituting N-methoxyamine hydrochloride for N-phenylhydroxyl amine hydrochloride, the title compound is obtained.

EXAMPLE 29

N-Ethoxy-N-ethyldecaneamide

Following the procedure of Example 7 except substituting ethoxylamine hydrochloride for benzylhydroxylamine hydrochloride in Part A and substituting ethyl iodide for methyl iodide in Part B, the title compound is obtained.

EXAMPLE 30

N-propoxy-N-butyldecaneamide

Following the procedure of Example 7 except substituting propoxylamine hydrochloride for benzylhydroxylamine hydrochloride in Part A and substituting butyl iodide for methyl iodide in Part B, the title compound is obtained.

EXAMPLE 31

N-Pentoxy-N-ethyldecaneamide

Following the procedure of Example 7 except substituting pentoxylamine hydrochloride for benzylhydroxylamine hydrochloride in Part A and substituting ethyl iodide for methyl iodide in Part B, the title compound is obtained.

EXAMPLE 32

N-Hexyloxy-N-propyldecaneamide

Following the procedure of Example 7 except substituting hexyloxylamine hydrochloride for benzylhydroxylamine hydrochloride in Part A and substituting propyl iodide for methyl iodide in Part B, the title compound is obtained.

EXAMPLE 33

N-Ethoxy-N-benzyldecaneamide

Following the procedure of Example 7 except substituting ethoxylamine hydrochloride for benzylhydroxylamine hydrochloride in Part A and substituting benzyl iodide for methyl iodide in Part B, the title compound is obtained.

EXAMPLE 34

N-Propoxy-N-phenethyldecaneamide

Following the procedure of Example 7 except substituting propoxylamine hydrochloride for benzylhydroxylamine hydrochloride in Part A and substituting phenethyl iodide for methyl iodide in Part B, the title compound is obtained.

EXAMPLE 35

N-Butoxy-N-pentyldecaneamide

Following the procedure of Example 7 except substituting butoxylamine hydrochloride for benzylhydroxylamine hydrochloride in Part A and substituting n-pentyl iodide for methyl iodide in Part B, the title compound is obtained.

EXAMPLE 36

N-Ethoxydecaneamide

Following the procedure of Example 7 except substituting ethoxylamine hydrochloride for benzylhydroxylamine hydrochloride in Part A and eliminating Step B, the title compound is obtained.

EXAMPLE 37

N-Propoxydecaneamide

Following the procedure of Example 7 except substituting propoxylamine hydrochloride for benzylhydroxylamine hydrochloride in Part A and eliminating Step B, the title compound is obtained.

EXAMPLE 38

N-Methoxy-N-methyldecaneamide

Following the procedure of Example 7 except substituting methoxylamine hydrochloride for benzylhydroxylamine hydrochloride in Part A, and eliminating Step C, the title compound is obtained.

EXAMPLE 39

N-ethoxy-N-ethyl(1-decenyl)amide

Following the procedure of Example 7 except substituting ethoxylamine hydrochloride for benzylhydroxylamine hydrochloride in Part A, substituting ethyl iodide for methyl iodide in Part B, and eliminating Step C, the title compound is obtained.

EXAMPLE 40

N-Propoxy-N-butyl(1-decenyl)amide

Following the procedure of Example 7 except substituting propoxylamine hydrochloride for benzylhydroxylamine hydrochloride in Part A, substituting butyl iodide for methyl iodide in Part B, and eliminating Step C, the title compound is obtained.

EXAMPLE 41

N-Pentoxy-N-ethyl(1-decenyl)amide

Following the procedure of Example 7 except substituting pentoxylamine hydrochloride for benzylhydroxylamine hydrochloride in Part A, substituting ethyl iodide for methyl iodide in Part B, and eliminating Step C, the title compound is obtained.

EXAMPLE 42

N-Hexyloxyl-N-n-propyl(1-decenyl)amide

Following the procedure of Example 7 except substituting hexyloxylamine hydrochloride for benzylhydroxylamine hydrochloride in Part A, substituting propyl iodide for methyl iodide in Part B, and eliminating Step C, the title compound is obtained.

EXAMPLE 43

N-Ethoxy-N-benzyl(1-decenyl)amide

Following the procedure of Example 7 except substituting ethoxylamine hydrochloride for benzylhydroxylamine hydrochloride in Part A, substituting benzyl iodide for methyl iodide in Part B, and eliminating Step C, the title compound is obtained.

EXAMPLE 44

N-Methoxy-N-phenethyl(1-decenyl)amide

Following the procedure of Example 7 except substituting methoxylamine hydrochloride for benzylhydroxylamine hydrochloride in Part A, substituting phenethyl iodide for methyl iodide in Part B, and eliminating Step C, the title compound is obtained.

EXAMPLE 45

N-Methoxy-N-ethyl(1-decenyl)amide

Following the procedure of Example 7 except substituting methoxylamine hydrochloride for benzylhydroxylamine hydrochloride in Part A, substituting ethyl iodide for methyl iodide in Part B, and eliminating Step C, the title compound is obtained.

EXAMPLE 46

N-Ethoxy(1-decenyl)amide

Following the procedure of Example 7 except substituting ethoxyamine hydrochloride for benzylhydroxylamine hydrochloride in Part A, and eliminating Steps B and C, the title compound is obtained.

EXAMPLE 47

N-Hydroxy-N-methylundecaneamide

Following the procedure of Example 7 except substituting 1-undecenylcarboxylic acid for 1-decenylcarboxylic acid in Part A, the title compound is obtained.

EXAMPLE 48

N-Hydroxy-N-methylhexylamide

Following the procedure of Example 7 except substituting 1-hexenylcarboxylic acid for 1-decenylcarboxylic acid, the title compound is obtained.

EXAMPLE 49

N-Hydroxy-N-methylheptaneamide

Following the procedure of Example 7 except substituting 1-heptenylcarboxylic acid for 1-decenylcarboxylic acid, the title compound is obtained.

EXAMPLE 50

N-Hydroxy-N-methyloctaneamide

Following the procedure of Example 7 except substituting 1-octenylcarboxylic acid for 1-decenylcarboxylic acid, the title compound is obtained.

EXAMPLE 51

N-Hydroxy-N-methylnonaneamide

Following the procedure of Example 7 except substituting 1-nonenylcarboxylic acid for 1-decenyl carboxylic acid, the title compound is obtained.

EXAMPLE 52

N-Hydroxy-N-methyldodecaneamide

Following the procedure of Example 7 except substituting 1-dodecenylcarboxylic acid for 1-decenylcarboxylic acid, the title compound is obtained.

EXAMPLE 53

N-Hydroxy-N-methylpentadecaneamide

Following the procedure of Example 7 except substituting 1-pentadecenylcarboxylic acid for 1-decenylcarboxylic acid, the title compound is obtained.

EXAMPLE 54

N-Hydroxy-N-methylpropaneamide

Following the procedure of Examples 7 and 13 except substituting acrylic acid for 1-decenylcarboxylic acid, the title compound is obtained.

EXAMPLE 55

N-Hydroxy-N-methyl(1-hexenyl)amide

Following the procedure of Example 8 except substituting (1-hexenyl)carboxylic acid for (1-decenyl)carboxylic acid in Part A and substituting methyl iodide for ethyl-4-iodobutyrate in Part B, the title compound is obtained.

EXAMPLE 56

4-[(Decylcarbonyl)hydroxyamino]butanoic acid

Following the procedure of Example 7 except substituting ethyl-4-iodobutyrate for methyl iodide, the title compound is obtained.

EXAMPLE 57

5-[[(1-Decenyl)carbonyl]hydroxyamino]pentanoic acid

Following the procedure of Example 8 except substituting ethyl-5-iodovalerate for ethyl-4-iodobutyrate, the title compound is obtained.

EXAMPLE 58

5-[[(1-Heptenyl)carbonyl]methoxyamino]pentanoic acid

Following the procedure of Example 12 except substituting 1-heptenylcarboxylic acid for 1-decenylcarboxylic acid, and ethyl-5 iodovalerate for ethyl-4-iodobutyrate and eliminating the addition of dicyclohexylamine, the title compound is obtained.

EXAMPLE 59

4-[[(1-Nonenyl)carbonyl]methoxyamino]butanoic acid

Following the procedure of Example 12 except substituting 1-nonenylcarboxylic acid for 1-decenylcarboxylic acid and eliminating the addition of dicyclohexylamine, the title compound is obtained.

EXAMPLE 60

5-[[(1-Undecenyl)benzoyl]methoxyamino]pentanoic acid

Following the procedure of Example 12 except substituting 1-undecenylcarboxylic acid for 1-decenylcarboxylic acid and ethyl-5 iodovalerate for ethyl-4-iodobutyrate and eliminating the addition of dicyclohexylamine, the title compound is obtained.

EXAMPLE 61

4-[[(1-Tridecyl)carbonyl]methoxyamino]butanoic acid

Following the procedure of Example 12 except substituting 1-tridecenylcarboxylic acid for 1-decenylcarboxylic acid, and eliminating the addition of dicyclohexylamine, the title compound is obtained.

EXAMPLE 62

3-[[(1-Hexenyl)carbonyl]ethoxyamino]pentanoic acid

Following the procedure of Example 12 except substituting 1-hexenylcarboxylic acid for 1-decenylcarboxylic acid, ethoxyamine hydrochloride for methoxyamine hydrochloride and ethyl-3 iodovalerate for ethyl-4-iodobutyrate, and eliminating the addition of dicyclohexylamine, the title compound is obtained.

EXAMPLE 63

4-[[(1-Octadecenyl)carbonyl]hexyloxyamino]butanoic acid

Following the procedure of Example 12 except substituting 1-octadecenylcarboxylic acid for 1-decenylcarboxylic acid and hexyloxyamine hydrochloride for methoxyamine hydrochloride, and eliminating the addition of dicyclohexylamine, the title compound is obtained.

EXAMPLE 64

(N-Hydroxydodecaneamido)acetic acid

Following the procedure of Example 15 except substituting 1-dodecenylcarboxylic acid for 1-decenylcarboxylic acid, the title compound is obtained.

EXAMPLE 65

(N-Hydroxyhexaneamido)acetic acid

Following the procedure of Example 15 except substituting 1-hexenylcarboxylic acid for 1-decenylcarboxylic acid, the title compound is obtained.

EXAMPLE 66

(N-Hydroxytetradecaneamido)acetic acid

Following the procedure of Example 15 except substituting 1-tetradecenylcarboxylic acid for 1-decenylcarboxylic acid, the title compound is obtained.

EXAMPLE 67

(N-hydroxylheptaneamido)acetic acid

Following the procedure of Example 15, except substituting 1-heptenylcarboxylic acid for 1-decenylcarboxylic acid, the title compound is obtained.

EXAMPLE 68

N-(4-Amino-4-oxobutyl)-N-methoxy octaneamide

Following the procedure of Example 13 except substituting 1-octenylcarboxylic acid for 1-decenylcarboxylic acid and methoxylamine hydrochloride for benzyloxylamine hydrochloride (in Example 7 Part A), the title compound is obtained.

EXAMPLE 69

N-(4-Amino-4-oxobutyl)-N-ethoxy tridecaneamide

Following the procedure of Example 13 except substituting 1-tridecenylcarboxylic acid for 1-decenylcarboxylic acid and ethoxylamine hydrochloride for benzyloxylamine hydrochloride (in Example 7 Part A), the title compound is obtained.

EXAMPLE 70

N-(4-Amino-4-oxobutyl)-N-methoxy decaneamide

Following the procedure of Example 13 except substituting methoxylamine hydrochloride for benzyloxylamine hydrochloride (in Example 7, Part A), the title compound is obtained.

EXAMPLE 71

N-(4-Amino-4-oxobutyl)-N-hydroxy undecaneamide

Following the procedure of Example 13 except substituting 1-undecenylcarboxylic acid for 1-decenylcarboxylic acid, the title compound is obtained.

EXAMPLE 72

N-(4-Amino-4-oxobutyl)-N-hydroxy nonadecaneamide

Following the procedure of Example 13 except substituting 1-nonadecenylcarboxylic acid for 1-decenylcarboxylic acid, the title compound is obtained.

EXAMPLE 73

N-Hydroxy(1-decenyl)amide

To a solution of compound prepared as described in Example 8 Part A (257 mg, 1 mmol) in 6 ml of CH₃OH under argon is added pyridinium 4-toluenesulfonate (210 mg, 1.0 eq.). The mixture is heated to 55° C. and stirred for 4 hours. The solution is diluted with ether and washed with ½ saturated sodium chloride (20 ml) and brine (10 ml). The organic layer is dried over anhydrous MgSO₄ and reduced to yield a solid. Recrystallization from hexane/EtOAc gives title compound.

EXAMPLE 74

N-Hydroxydecaneamide

Following the procedure of Example 7 Part C except substituting the Example 73 compound for the Example 7 Part B compound, the title compound is obtained.

EXAMPLE 75

N-Hydroxy(1-Tetradecenyl)amide

Following the procedure of Example 73 except substituting 1-tridecenylcarboxylic acid for 1-decenylcarboxylic acid in Example 7, Part A, the title compound is obtained.

EXAMPLE 76

N-Hydroxy-N-allyl-benzenebutanamide

Following the procedure of Example 6 except substituting allyl bromide for pentyl bromide, the title compound is obtained.

EXAMPLE 77

N-Hydroxy-N-cyclohexylbenzenebutanamide

Following the procedure of Example 3 except substituting N-cyclohexylhydroxylamine hydrochloride for N-phenylhydroxylamine hydrochloride, the title compound is obtained.

EXAMPLE 78

N-Hydroxy-N-methyl-4-cyclohexylbutaneamide

Following the procedure of Example 3 except substituting 3-cyclohexylpropylcarboxylic acid for 3-phenylpropylcarboxylic acid in Part A, the title compound is obtained.

What is claimed is:

1. A compound having the structure

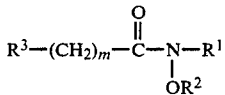

wherein m is 1 to 5, $R^1$ is lower alkyl, phenylalkyl or phenyl, $R^2$ is H or lower alkyl; and $R^3$ is cycloalkyl, phenyl or biphenyl, all of the above hydrocarbon groups being unsubstituted.

2. The compound as defined in claim 1 wherein $R^1$ is $CH_3$, $t\text{-}C_4H_9$, $C_5H_{11}$, phenyl or benzyl.

3. The compound as defined in claim 1 wherein $R^1$ is phenyl or phenylalkyl, $R^2$ is H, and $R^3$ is phenyl, biphenyl, or cycloalkyl and m is 1, 2 or 3.

4. The compound as defined in claim 1 having the name N-hydroxy-N-methyl [1,1'-biphenylyl]-4-acetamide.

5. The compound as defined in claim 1 having the name N-(1,1'-dimethylethyl)-N-hydroxy[1,1'-biphenylyl]-4-acetamide.

6. The compound as defined in claim 1 having the name N-hydroxy-N-phenylbenzenebutanamide.

7. The compound as defined in claim 1 having the name N-hydroxy-N-(phenylmethyl)cyclohexane acetamide.

8. The compound as defined in claim 1 having the name N-hydroxy-N-(phenylmethyl)benzenebutanamide.

9. The compound as defined in claim 1 having the name N-hydroxy-N-pentylbenzenebutanamide.

10. A composition for inhibiting allergic conditions in a mammalian species, comprising an effective amount of a compound as defined in claim 1 or a pharmaceutically acceptable salt thereof, and a pharmaceutically acceptable carrier thereof.

11. A method of inhibiting $\Delta^5$-lipoxygenase which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A method for treating asthma in a mammalian species in need of such treatment, which comprises administering to a mammalian host an effective amount of a compound as defined in claim 1 or a pharmaceutically acceptable salt thereof.

* * * * *